US012685868B2

(12) United States Patent
Midgett et al.

(10) Patent No.: US 12,685,868 B2
(45) Date of Patent: Jul. 21, 2026

(54) IMPLANTABLE MEDICAL DEVICE CONFIGURED TO PROVIDE AN INTRA-CARDIAC FUNCTION

(71) Applicant: BIOTRONIK SE & Co. KG, Berlin (DE)

(72) Inventors: Madeline Anne Midgett, Portland, OR (US); Daniel Young, Portland, OR (US); Christopher Jones, Oregon City, OR (US); R. Hollis Whittington, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 414 days.

(21) Appl. No.: 18/261,910

(22) PCT Filed: Jan. 28, 2022

(86) PCT No.: PCT/EP2022/052068
§ 371 (c)(1),
(2) Date: Jul. 18, 2023

(87) PCT Pub. No.: WO2022/167340
PCT Pub. Date: Aug. 11, 2022

(65) Prior Publication Data
US 2024/0075299 A1     Mar. 7, 2024

Related U.S. Application Data

(60) Provisional application No. 63/145,643, filed on Feb. 4, 2021.

(30) Foreign Application Priority Data

Feb. 17, 2021    (EP) .................................... 21157618

(51) Int. Cl.
*A61N 1/36* (2006.01)
*A61N 1/02* (2006.01)
(Continued)

(52) U.S. Cl.
CPC ............. *A61N 1/365* (2013.01); *A61N 1/025* (2013.01); *A61N 1/3756* (2013.01)

(58) Field of Classification Search
CPC ...... A61N 1/365; A61N 1/025; A61N 1/3756; A61N 1/3704
See application file for complete search history.

(56) References Cited

U.S. PATENT DOCUMENTS 6,195,584 B1    2/2001  Hill et al.
9,008,760 B2 *  4/2015  Dong ................... A61B 5/0245
                                                           600/509
(Continued)

FOREIGN PATENT DOCUMENTS

JP          2014525762 A    10/2014
JP          2019519326 A    7/2019

OTHER PUBLICATIONS

International Search Report (PCT/ISA/210) and Written Opinion (PCT/ISA/237) mailed on Jul. 13, 2023, by the European Patent Office as the International Searching Authority for International Application No. PCT/EP2022/052068. (8 pages).
(Continued)

*Primary Examiner* — Rex R Holmes
(74) *Attorney, Agent, or Firm* — Buchanan Ingersoll & Rooney PC

(57)                    ABSTRACT
An implantable medical device configured to provide for an intracardiac function, the implantable medical device comprises a body, a sensor arrangement arranged on the body and configured to receive cardiac sense signals, and a processing circuitry operatively connected to the sensor
(Continued)

arrangement. The processing circuitry is configured to process cardiac sense signals received using the sensor arrangement to detect a signal deflection potentially indicative of an atrial event caused by atrial activity to obtain an atrial detection, to detect a signal deflection indicative of a ventricular event caused by ventricular activity succeeding said atrial detection, to determine an atrial-ventricular interval representing a time between the atrial detection and the ventricular event, and to identify the atrial detection as valid or invalid based on the atrial-ventricular interval.

14 Claims, 5 Drawing Sheets

(51) Int. Cl.
   A61N 1/365        (2006.01)
   A61N 1/375        (2006.01)

(56)                   References Cited

U.S. PATENT DOCUMENTS

| | | | |
|---|---|---|---|
| 9,592,392 | B2 | 3/2017 | Demmer et al. |
| 2007/0078488 | A1 | 4/2007 | Björling et al. |
| 2012/0330379 | A1 | 12/2012 | Higham et al. |
| 2013/0138006 | A1 | 5/2013 | Bornzin et al. |
| 2018/0021581 | A1 | 1/2018 | An et al. |
| 2019/0308021 | A1 | 10/2019 | Demmer et al. |
| 2021/0023377 | A1 | 1/2021 | Muessig |
| 2022/0168575 | A1* | 6/2022 | Greenhut ........... A61N 1/36578 |

OTHER PUBLICATIONS

Office Action for Japanese Patent Application No. 2023-535626 dated Jul. 14, 2025 (with English Translation).

* cited by examiner

IMPLANTABLE MEDICAL DEVICE CONFIGURED TO PROVIDE AN INTRA-CARDIAC FUNCTION

CROSS-REFERENCE TO RELATED APPLICATIONS

This application is the United States National Phase under 35 U.S.C. § 371 of PCT International Patent Application No. PCT/EP2022/052068, filed on Jan. 28, 2022, which claims the benefit of European Patent Application No. 21157618.6, filed on Feb. 17, 2021 and U.S. Provisional Patent Application No. 63/145,643, filed on Feb. 4, 2021, the disclosures of which are hereby incorporated by reference herein in their entireties.

TECHNICAL FIELD

The instant invention generally relates to an implantable medical device for providing an intracardiac function, in particular a pacing function such as ventricular pacing, specifically a VDD pacing.

BACKGROUND

In an implantable medical device, e.g., in the shape of a leadless pacemaker device or a cardiac stimulation device using a subcutaneously implanted pulse generator and one or multiple leads extending into a patient's heart, it may be desirous to provide a stimulation in a ventricle of the patient's heart, e.g., in the right ventricle, in synchrony with an atrial activity. For this, a ventricular pacing action shall take into account atrial sense signals to control the ventricular pacing based on atrial events indicative of atrial activity, for example, in a so-called VDD pacing mode.

In recent years, leadless pacemakers have received increasing attention. Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

A leadless pacemaker or a lead of a stimulation device may specifically be designed for implantation in the right ventricle and, in this case, during implant is placed, e.g., in the vicinity of the apex of the right ventricle. Ventricular pacing may, for example, be indicated in case a dysfunction at the AV node occurs, but the sinus node function is intact and appropriate. In such a case in particular a so-called VDD pacing may be desired, involving ventricular pacing with atrial tracking and hence requiring sensing of atrial activity in order to a pace the ventricle based on intrinsic atrial contractions.

VDD pacing is in particular motivated by patient hemodynamic benefits of atrioventricular (AV) synchrony by utilizing an appropriate sinus node function to trigger ventricular pacing, is potentially allowing to maximize ventricular preload, to limit AV valve regurgitation, to maintain low mean atrial pressure, and to regulate autonomic and neurohumoral reflexes.

Publications have explored solutions to use modalities to detect mechanical events of atrial contractions, including the sensing of motion, sound and pressure (see, for example, U.S. Publication No. 2018/0021581 A1 disclosing a leadless cardiac pacemaker including a pressure sensor and/or an accelerometer to determine an atrial contraction timing). As mechanical events generally exhibit a small signal volume, signal detection based on mechanical events, for example, motion, sound or pressure, may be difficult to sense, in particular when the implantable medical device is placed in the ventricle and hence rather far removed from the atrium of which contractions shall be sensed. In addition, wall motion and movement of blood generated by atrial contractions may not be directly translated to the ventricle, and cardiac hemodynamic signals, such as motion, heart sounds and pressure, are likely affected by external factors such as posture and patient activity.

An additional disadvantage of mechanical sensing may result from the signal merging with ventricular activity signals at lower rates than is possible with electrical sensing.

The present disclosure is directed toward overcoming one or more of the above-mentioned problems, though not necessarily limited to embodiments that do.

SUMMARY

It is an object to provide an implantable medical device and a method for operating an implantable medical device allowing, in particular, for ventricular pacing with atrioventricular synchrony, hence requiring a reliable sensing of atrial events in order to provide for a ventricular pacing based on such atrial events.

Such desires are addressed by an implantable medical device configured to provide for an intracardiac function having the features of claim 1.

In one aspect, an implantable medical device configured to provide for an intracardiac function comprises: a body; a sensor arrangement arranged on the body and configured to receive cardiac sense signals; and a processing circuitry operatively connected to the sensor arrangement. The processing circuitry is configured to process cardiac sense signals received using the sensor arrangement to detect a signal deflection potentially indicative of an atrial event caused by atrial activity to obtain an atrial detection, to detect a signal deflection indicative of a ventricular event caused by ventricular activity succeeding said atrial v, to determine an atrial-ventricular interval representing a time between the atrial detection and the ventricular event, and to identify the atrial detection as valid or invalid based on the atrial-ventricular interval.

Within the implantable medical device, processing circuitry is used to process and analyze cardiac sense signals in order to detect atrial events which are indicative of atrial activity. Generally, for detecting atrial events a scheme may be employed in which a cardiac sense signal is compared to a threshold in a suitable sense window for sensing atrial activity, and in the case of a threshold crossing an atrial event is assumed. However, as the sensing may take place in the ventricle by means of the sensor arrangement placed on the device body implanted in the ventricle, atrial activity takes place in the far-field and hence atrial sense signals are received at the sensor arrangement as far-field signals having a comparatively small signal amplitude. Therefore there is a risk of oversensing near-field signals, in particular relating to ventricular activity, such as the QRS waveform in an intracardiac electrogram (IEGM).

In particular, if the sensor arrangement is an electrode arrangement for sensing electrical IEGM signals, the beginning of a QRS waveform (due to signals in the near-field and caused by ventricular activity) may be mistaken for atrial sense signals, such that an atrial detection may be falsely identified as an atrial event determined based on a threshold crossing by signals relating to a QRS waveform.

For this reason, it is proposed to assume an atrial detection as valid if and only if it occurs at a substantial timing duration with respect to a subsequent ventricular event. When processing cardiac sense signals it hence is determined whether a signal deflection in the cardiac sense signal may indicate an atrial event. Subsequently, a ventricular event is detected, and an atrial-ventricular interval indicating the timing duration in between the assumed atrial event and the subsequent ventricular event is determined. The atrial-ventricular interval then is evaluated, and based on the atrial-ventricular interval it is determined whether the atrial detection is valid or invalid. In this way, in particular, it may be determined whether the atrial event is detected at a sufficient duration from the subsequent ventricular event, and only if this is the case the atrial event is assumed as a true, valid atrial event. Otherwise, the presumed atrial event is classified as invalid, as the atrial detection possibly may lie too close to the succeeding ventricular event and hence may be caused, for example, by the beginning of a cardiac sense signal waveform due to ventricular activity, e.g., the QRS waveform in an intracardiac electrogram.

The sensor arrangement in particular may be formed by an electrode arrangement of one or multiple electrodes arranged on the body. Hence, by means of the sensor arrangement electrical signals may be received, such electrical signals representing intracardiac electrogram recordings and hence being indicative of cardiac activity.

In another embodiment, the sensor arrangement may be configured for sensing cardiac signals in the shape of pressure signals, acoustic signals, ultrasound signals, motion signals and/or impedance signals.

In one embodiment, the body of the implantable medical device may be formed by a lead which is connectable to a generator of the implantable medical device. In this case, the generator may be implanted into a patient, for example, subcutaneously remote from the heart, the lead forming the body extending from the generator into the heart such that the body with the sensor arrangement arranged thereon is placed in the heart, for example, within the right ventricle in order to engage with tissue at the right ventricle.

In another embodiment, the body may be formed by a housing of a leadless pacemaker device. In this case, the implantable medical device is formed as a leadless device, which does not comprise leads extending from a location outside of the heart into the heart for is providing for a stimulation and/or sensing within the heart. The housing of the leadless pacemaker device may be placed on tissue with a distal end formed by the housing, the sensor arrangement, e.g., being placed (at least in part) on or in the vicinity of the distal end and engaging with tissue when placing the leadless pacemaker device on tissue with its distal end.

If the implantable medical device is a leadless pacemaker device, the housing provides for an encapsulation of the implantable medical device, the implantable medical device including all required components for self-sufficient operation, such as the processing circuitry, an energy storage such as a battery, electric and electronic circuitry and the like, within the housing. The housing is fluid-tight such that the implantable medical device may be implanted into cardiac tissue and may be kept in cardiac tissue over an extended period of time to provide for a long-term, continuous cardiac pacing operation.

In one embodiment, the processing circuitry is configured to compare the atrial-ventricular interval to an exclusion interval and to identify the atrial detection as valid if the atrial-ventricular interval is larger than the exclusion interval. Alternatively, if the atrial-ventricular interval is smaller than the exclusion interval, the atrial detection is identified as invalid. This is based on the finding that detected atrial events that are too close to a subsequent ventricular event likely are due to signals having a non-atrial origin, such as ventricular near-field signals, for example, the beginning of a QRS waveform in an intracardiac electrogram. A timing distance with respect to a subsequent ventricular event hence may be used to disqualify and discard a presumed atrial event, which likely is falsely detected. For disqualifying the atrial detection, herein, the timing between the atrial detection and the subsequent ventricular event—that is the atrial-ventricular interval—is compared to a threshold, namely the atrial exclusion interval. Only if the time distance between the atrial detection and the subsequent ventricular event is larger than the exclusion interval, the atrial detection is assumed as valid. Otherwise, the atrial detection is assumed as invalid.

This criterion(s) for determining the atrial event is particularly simple in comparison to those in methods from the prior art. It is therefore particularly suitable for use in a leadless pacemaker, for which resource-saving algorithms are advantageous.

In one embodiment, the processing circuitry is configured to determine a peak amplitude associated with the atrial event if the atrial detection is identified as valid. If the atrial detection is identified as valid, data recorded for the atrial event is analyzed in order to determine the peak amplitude. For example, the atrial event is identified as that point in time at which the cardiac sense signal crosses a sense threshold, also denoted as atrial detection threshold. Beginning with the crossing of the sense threshold a peak detection window is started, and within the peak detection window the largest signal amplitude value is assumed as that detection's peak amplitude.

In one embodiment, the processing circuitry is configured to determine whether the peak detection window overlaps with the exclusion interval. The peak detection window may, for example, have a fixed length. If the peak detection window overlaps with the exclusion interval, which precedes the subsequent ventricular event and ends with the ventricular event, data associated with the overlapping portion of the peak detection window is discarded and is not used for determining the peak amplitude. This is based on the assumption that a cardiac sense signal portion within the exclusion interval potentially is not associated with atrial activity, but, for example, with near-field signals due to ventricular activity, such that this signal portion should be discarded and should not be processed for analyzing atrial activity.

The exclusion interval may lie in a range between 0 ms and 175 ms.

The exclusion interval may be programmed as a fixed value. Alternatively, the exclusion interval may be adaptive and may depend, for example, on the actual heart rate or an average heart rate or on an activity parameter indicating activity of the patient.

Using the peak amplitude, the processing circuitry may be configured to update a sense threshold for detecting a subsequent atrial event. In particular, the processing circuitry may be configured to update the sense threshold using an average threshold reference and a percentage ratio according to the formula $$ST(t)=PC \cdot ATR(t),$$

where ST is the current sense threshold for cycle t, PC is a percentage ratio, and ATR(t) is the current average threshold reference for cycle t. The percentage ratio may lie, for example, in the range between 0% and 100%.

It shall be noted that the equation above may be used to set the sense threshold in some or all cycles, wherein however also a more complicated scheme, including, for example, a step-down technique for adapting the sense threshold, may be employed.

The average threshold reference may be computed and updated based on the peak amplitude according to the following equation:

$$ATR(t)=W \cdot PA(t-1)+(1-W) \cdot ATR(t-1),$$

where W indicates an update weight which determines how much the average threshold reference should change based on the previous peak amplitude, PA(t−1) is the peak amplitude as determined for the previous cycle t−1, and ATR(t−1) is the previous average threshold reference. For the actual cycle t the average threshold reference hence is determined based on the previously determined valid peak amplitude and on the previous average threshold reference for cycle t−1. For each cycle, hence, the average threshold reference is updated and computed anew, such that the average threshold reference is dynamically adjusted on a cycle-by-cycle basis.

The peak amplitude is determined only for those atrial detections which are qualified as valid based on the comparison of the atrial-ventricular interval with, e.g., an exclusion interval. If an atrial detection is classified as invalid, the peak amplitude is not determined, and the average threshold reference is not updated. In this case, the cycle is counted as a missed cycle, i.e., a cycle in which no atrial activity was sensed. In this way, it in particular is prevented that a false detection of an atrial event, for example, due to near-field signals such as the beginning of a QRS waveform in an intracardiac electrogram, may falsely lead to an increase in the average threshold reference used to set the sense threshold in the next cycle.

In one embodiment, the processing circuitry comprises a first processing channel having a first gain for processing a first processing signal derived from sensor signals received via the sensor arrangement and a second processing channel having a second gain for processing a second processing signal derived from sensor signals received via the sensor arrangement, the second gain being higher than the first gain.

Generally, the implantable medical device may be configured to process different processing signals. For obtaining such processing signals, a sensor arrangement is provided, the sensor arrangement comprising, e.g., one or multiple electrodes to receive electrical signals from which the processing signals are derived. The processing signals herein, for example, may be obtained from each using a pair of electrodes, wherein for obtaining the different processing signals the same pair of electrodes or different pairs of electrodes may be used. In the first case, a single electrical signal, such as an intracardiac electrogram, may be obtained, from which different processing signals, namely the first processing signal and the second processing signal are derived for separate processing. In the latter case, separate electrical signals relating, for example, to a ventricular sensing signal and an atrial sensing signal (i.e., by applying a sensing optimized for atrial sensing) may be received in order to derive the first processing signal and the second processing signal from such different electrical signals, the different electrical signals, for example, being received using different pairs of electrodes of the sensor arrangement.

The different processing signals, in one embodiment, are processed in different processing paths of the processing circuitry. For this, the processing circuitry comprises a first processing channel for processing the first processing signal, the first processing signal relating, for example, to a near-field (in particular ventricular) sensing signal which, according to the placement of the implantable medical device, for example, in a ventricle of a patient's heart, may be strong such that the first processing channel may exhibit a rather low gain.

In addition, the processing circuitry comprises a second processing channel for processing the second processing signal, which may relate, for example, to a far-field atrial sensing signal which, in case of a placement of the implantable medical device in the ventricle, may have a small amplitude, due to the distance between the location of implantation and the source of origin of the signals. In order to allow for a reliable processing of the second processing signal, the second processing channel exhibits a gain higher than the gain of the first processing channel, such that features relating to an atrial activity may be suitably analyzed within the received signals.

Because, for a placement of the implantable medical device in, for example, the ventricle, atrial activity occurs in the far field, atrial events within a regular ventricular sensing signal (for example, obtained be a regular ventricular QRS sensing channel) may be hard to discern, as a P wave stemming from atrial activity may exhibit a small amplitude in relation to QRS and T waves. For this reason, signal portions relating to far-field activity may be processed separately from signals relating to near-field activity within the second processing channel, such that within the second processing channel far-field events may be detected with increased reliability and enhanced timing precision.

The implantable medical device, in one aspect, is to be placed entirely or partially in the right or left ventricle.

In one aspect, the sensor arrangement is formed by an electrode arrangement, the electrode arrangement comprising a first electrode arranged in the vicinity of a tip of the body. The first electrode shall come to rest on cardiac tissue in an implanted state of the implantable medical device, such that the first electrode contacts cardiac tissue, e.g., at a location effective for injecting a stimulating signal into cardiac tissue for provoking a pacing action, in particular ventricular pacing.

In one aspect, the electrode arrangement comprises a second electrode formed by an electrode ring circumferentially extending about the body. Alternatively, the second electrode may, for example, be formed by a patch or another electrically conductive area formed on the body. The second electrode is placed at a distance from the tip of the body and hence at a distance from the first electrode arranged at the tip.

In one embodiment, the processing circuitry is configured to process, as said first processing signal, a first signal sensed between the first electrode and the second electrode. Such first signal may be denoted as near-field vector to be received between a pair of electrodes comprised of the first electrode and the second electrode. As the first electrode and the second electrode may, in one embodiment, be located at a rather close distance to each other, such pair of electrodes is predominantly suited to receive signals in close proximity to the implantable medical device, i.e., in the near-field region within the ventricle if the implantable medical device is implanted into the ventricle. The sense signal received in between the first electrode and the second electrode is provided to the first processing channel for processing in order to, for example, detect near-field (e.g., ventricular) events in the signal.

In one embodiment, the body comprises a remote location (e.g., the far end of a housing of a leadless pacemaker device) removed from the tip, the electrode arrangement comprising a third electrode arranged on the body at the remote location. The third electrode is operatively connected to the processing circuitry, such that the processing circuitry is enabled to receive and process signals received via the third electrode.

In one aspect, the processing circuitry is configured to process, as said second processing signal, a second signal sensed between the first electrode and the third electrode. Such second signal vector arising between the first electrode and the third electrode may be referred to as far-field vector, the first electrode and the third electrode exhibiting a distance with respect to each other larger than the first and the second electrode. The second signal may in particular be processed to detect events in the far-field, i.e., atrial contractions in case the implantable medical device is placed in the ventricle, such that by means of the second signal an intrinsic atrial activity prior to injecting a pacing stimulus may be captured.

The second signal sensed between the first electrode and the third electrode may be used to sense intrinsic atrial contractions in order to provide for an atrial-to-ventricular synchronization by timely injecting a stimulus at the ventricular location of implantation of the pacemaker device following atrial contractions. The second signal is provided to the second processing channel in order to process the signal and detect atrial events from the signal, in order to provide for a pacing action based on detected atrial events, hence allowing for a ventricular pacing with atrioventricular (AV) synchrony.

In one embodiment, the second processing channel comprises a processing stage for differentiating one wave portion from another wave portion in the second processing signal. The processing stage in particular may be configured to apply, to the second processing signal, at least one of a bandpass filtering, a blanking window for excluding a portion of the second signal from further processing, a moving average filtering, and a rectification. By means of the processing stage, in particular such wave portions shall be isolated and/or emphasized within the signal to be processed which may be indicative of, e.g., an atrial event. If the implantable medical device is placed in the ventricle of a patient's heart, signal portions relating to far-field atrial activity may have a much smaller amplitude than signal portions relating to a near-field ventricular activity. Hence, the processing serves to differentiate between the different signal portions in order to identify such signal portion which may contain signals relating to far-field atrial activity.

For isolating, e.g., the P wave in an intracardiac electrogram, a bandpass filtering may be applied, hence differentiating wave portions relating to the P wave from wave portions in particular relating to QRS and T waves stemming from ventricular activity. Alternatively or in addition, a blanking method may be applied in order to blank out certain portions of the second processing signal, namely such portions which contain signals stemming from events other than a far-field atrial activity. A blanking window, for this, serves to silence signal portions which are not of interest for far-field activity, but which may rather interfere with the detection of far-field activity. By means of a blanking window such portions of the signal which do not relate to far-field atrial activity hence are excluded from processing, such that the processing is limited to those signal portions (likely) relating to far-field activity. Alternatively or in addition, other methods such as a moving average filtering, finite to differences or a rectification of the signal may be applied. A moving averaging filter herein can be used to smooth the processing signal. Rectification can serve to easily compare the processed signal to a (single) threshold in order to identify when the signal magnitude exceeds a predefined threshold.

In one embodiment, the first processing channel comprises a first detection stage for detecting at least one near-field event in the first signal. Herein, the processing stage of the second processing channel may be configured to determine at least one limit of a blanking window for excluding a portion of the second signal from further processing based on a near-field (e.g., ventricular) event detected by the first detection stage of the first processing channel. The first processing channel serves to process a signal at a lower gain for detecting near-field events, i.e., events that are due to an activity in close proximity to the implanted implantable medical device, for example, in the ventricle in which the implantable medical device is implanted. As the near-field event will also be picked up in the second processing signal, it is advantageous to blank out such a signal portions relating to a near-field activity, i.e., QRS and T waves in in case of a placement of the implantable medical device in the ventricle. In order to correctly locate the blanking window, detected near-field events may be taken into account, in order to, for example, determine a regular timing in between atrial events and ventricular events. From detected near-field events it may be determined in what time range after a far-field event a near-field event typically should occur, such that the blanking window, defined by a start time and a stop at time, may be appropriately set to blank out such portions of the second processing signal which relates to the near-field ventricular events.

During the blanking window the second processing channel may, at least partially, be switched off in order to, for example, save power within the second, high gain processing channel. The second processing channel may, for example, comprise an amplification stage for amplifying the second processing signal, wherein the amplification stage may be switched off during the period of the blanking window such that that no power is consumed by amplification during the time interval of the blanking window.

A detection of far-field atrial events takes place in a detection window outside a blanking window. The detection window herein may start (immediately) at the end of a prior blanking window and may end at the beginning of the next blanking window. It however is also conceivable that the detection window, for example, starts at some time delay after the end of a prior blanking window. In between the end of the blanking window and the start of the detection window the second processing channel may be fully functional and process the associated second processing signal, wherein however a detection of far-field (atrial) events does not take place until the start of the detection window.

In one embodiment, the second processing channel comprises a second detection stage for detecting an atrial event in the second processing signal. The second detection stage may be arranged logically behind the processing stage of the second processing channel, such that the second detection stage receives processed signals from the processing stage of the second processing channel. The second detection stage herein serves to identify far-field atrial events in the second processing signal in order to output information relating to the timing of a detected atrial event.

The second detection stage of the second processing channel in particular may be configured to detect an atrial event by comparing the second processing signal to a sense threshold. In case the magnitude of the second processing signal exceeds the sense threshold, it may be concluded that a far-field atrial event is present. The processing herein may take place on a rectified signal, which makes it possible to apply a single threshold to which the rectified signal may be compared. It however is also possible to identify a far-field atrial event in a non-rectified signal, for example, by applying two thresholds, namely a positive threshold and a negative threshold, wherein a far-field atrial event is identified if the positive signal portion exceeds the positive threshold and/or the (magnitude of the) negative signal portion exceeds the negative threshold.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein.

DETAILED DESCRIPTION

Figure 1:
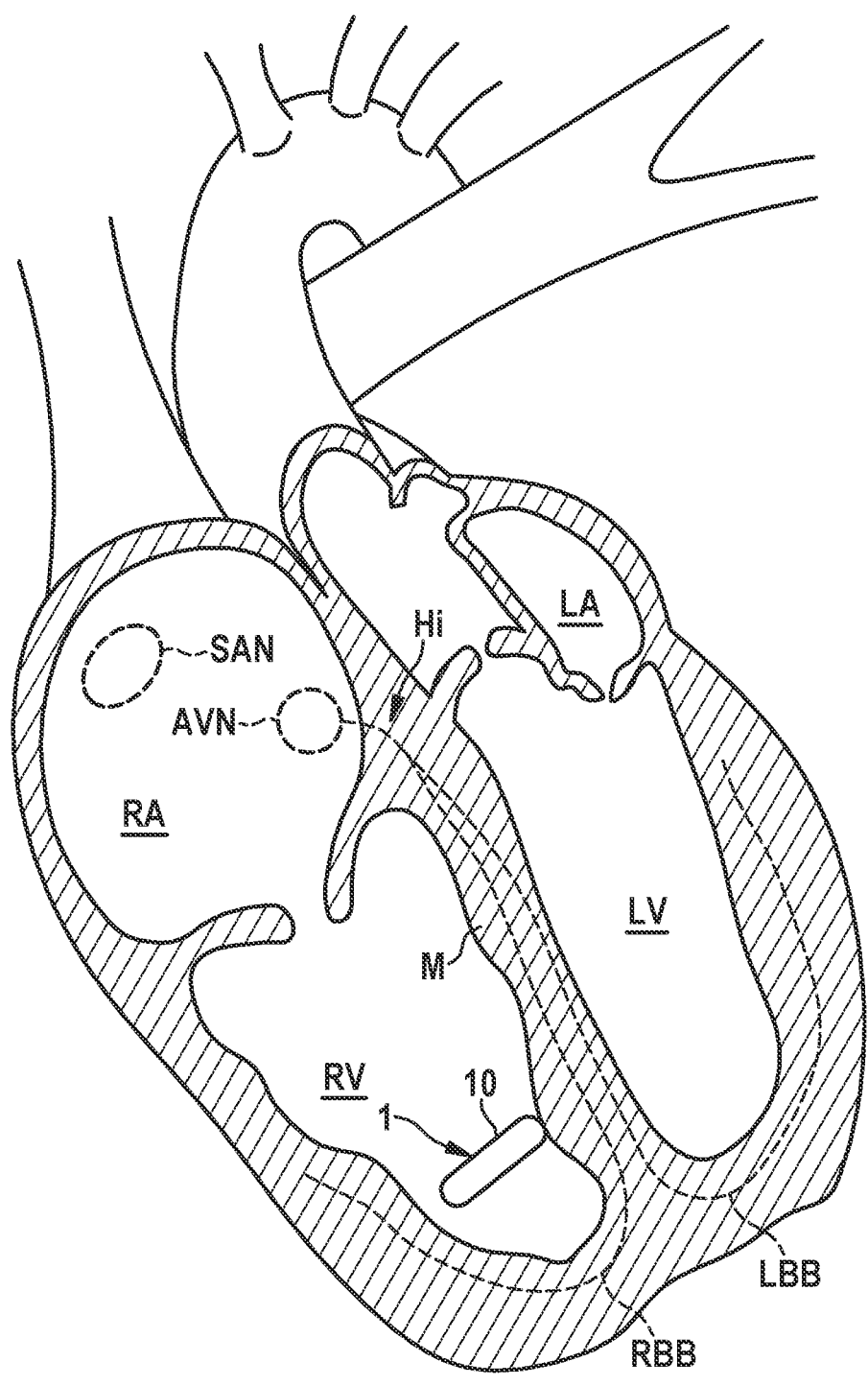
FIG. 1 shows a schematic view of the human heart, with an implantable medical device in the shape of a leadless pacemaker device implanted therein.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

In the instant invention it is proposed to provide an implantable medical device providing for an intracardiac function, in particular a ventricular pacing, specifically a so-called VDD pacing.

FIG. 1 shows, in a schematic drawing, the human heart comprising the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In case of a block at the atrioventricular node AVN, the intrinsic electrical conduction system of the heart H may be disrupted, causing a potentially insufficient intrinsic stimulation of ventricular activity, i.e., insufficient or irregular contractions of the right and/or left ventricle RV, LV. In such a case, a pacing of ventricular activity by means of a pacemaker device may be indicated, such pacemaker device stimulating ventricular activity by injecting stimulation energy into intracardiac tissue, specifically myocardium M.

In one embodiment, an implantable medical device 1 in the shape of a leadless cardiac pacemaker device, as schematically indicated in FIG. 1, is provided for a ventricular pacing action, the leadless pacemaker device having a body 10 formed by the housing of the leadless pacemaker device.

Figure 6:
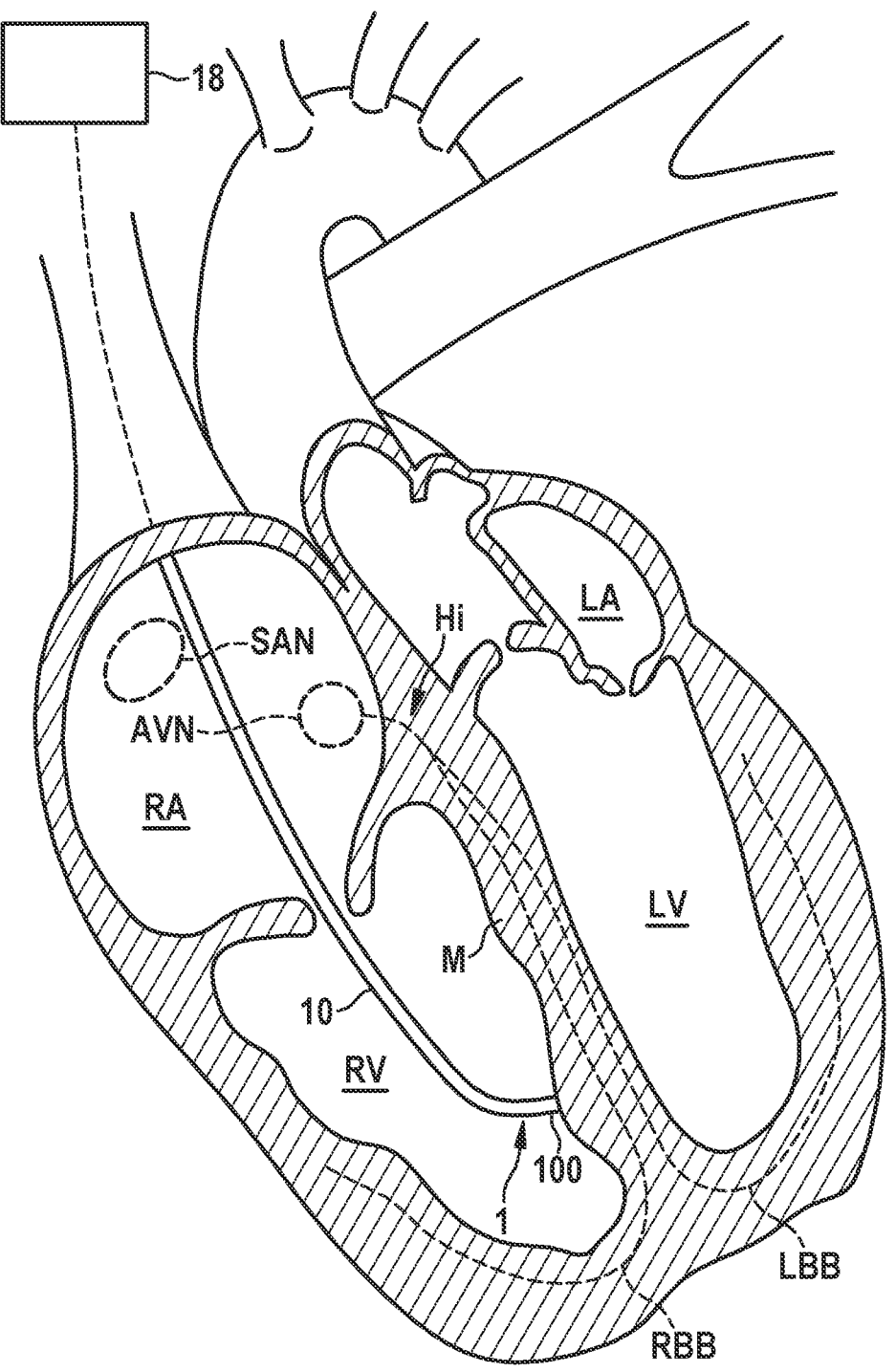
FIG. 6 shows a schematic view of the human heart, with an implantable medical device in the shape of cardiac stimulation device having a lead implanted in the right ventricle.

In another embodiment, as shown in FIG. 6, the implantable medical device 1 may be a stimulation device having a generator 18 and at least one lead forming a body 10 of the implantable medical device 1 and extending transvenously from the generator 18 into the patient's heart.

Whereas common implantable medical devices are designed to sense a ventricular activity by receiving electrical signals from the ventricle RV, LV they are placed in, it may be desirable to provide for a pacing action which achieves atrioventricular (AV) synchrony by providing a pacing in the ventricle in synchrony with intrinsic atrial activity. For such pacing mode, also denoted as VDD pacing mode, it is required to sense atrial activity and identify atrial events relating to atrial contractions in order to base a ventricular pacing on such atrial events.

Figure 3:
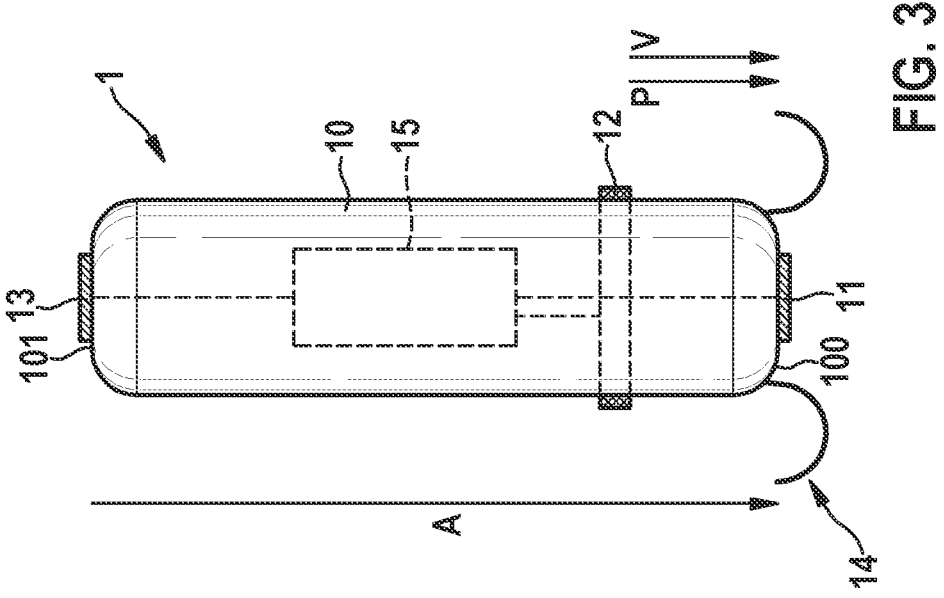
FIG. 3 shows a schematic view of an implantable medical device, indicating signal vectors between different electrodes of the implantable medical device.
Figure 2:
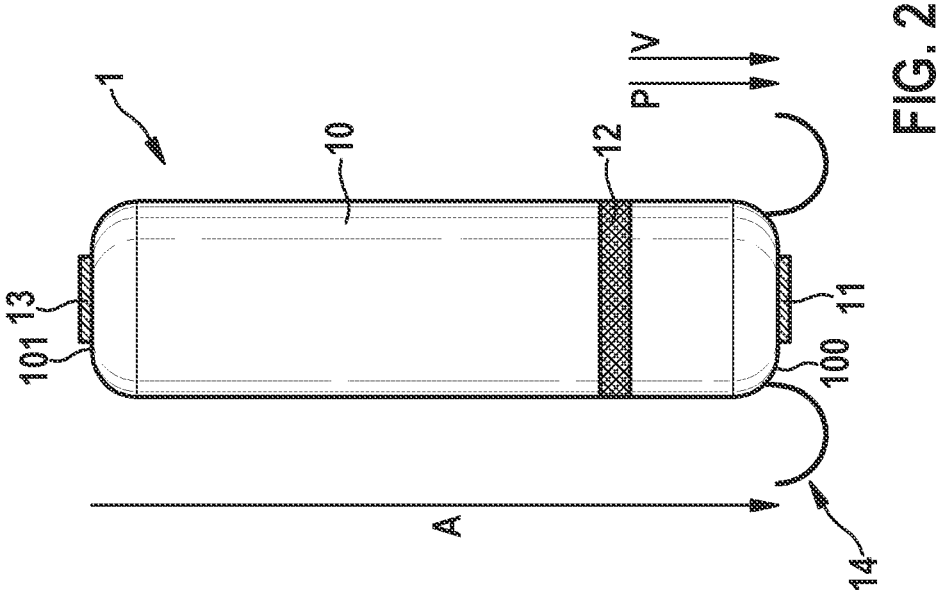
FIG. 2 shows a schematic view of an implantable medical device.

Referring now to FIGS. 2 and 3, in one embodiment an implantable medical device 1 in the shape of a leadless pacemaker device configured to provide for an intracardiac pacing, in particular in a VDD pacing mode, comprises a housing 10 enclosing electrical and electronic components for operating the implantable medical device 1. In particular, enclosed within the housing 10 is a processing circuitry 15, comprising, for example, also a communication interface for communicating with an external device, such as a programmer wand. In addition, electrical and electronic components such as an energy storage in the shape of a battery are confined in the housing 10. The housing 10 provides for an encapsulation of components received therein, the housing 10 having the shape of, e.g., a cylindrical shaft having a length of, for example, a few centimeters.

The implantable medical device 1 is to be implanted immediately on intracardiac tissue M. For this, the implantable medical device 1 comprises, in the region of a tip 100, a fixation device 14, for example, in the shape of nitinol wires to engage with intracardiac tissue M for fixedly holding the implantable medical device 1 on the tissue in an implanted state.

The implantable medical device 1 in the embodiment of FIGS. 2 and 3 does not comprise leads, but receives signals relating to a cardiac activity by means of an electrode arrangement arranged on the housing 10 and also emits stimulation signals by means of such electrode arrangement. In the embodiment of FIGS. 2 and 3, the implantable medical device 1 comprises different electrodes 11, 12, 13 making up the electrode arrangement and serving to emit pacing signals towards intracardiac tissue M for providing a pacing and to sense electrical signals indicative of a cardiac activity, in particular indicative of atrial and ventricular contractions.

A first electrode 11 herein is denoted as pacing electrode. The first electrode 11 is placed at a tip 100 of the housing 10 and is configured to engage with cardiac tissue M.

A second electrode 12 herein is denoted as pacing ring. The second electrode 12 serves as a counter-electrode for the first electrode 11, a signal vector P arising between the first electrode 11 and the second electrode 12 providing for a pacing vector P for emitting pacing signals towards the intracardiac tissue M.

In addition, the second electrode 12 serves as a sensing electrode for sensing signals, in particular relating to ventricular contractions, a signal vector V arising between the second electrode 12 and the first electrode 11, the signal vector V being denoted as near-field vector.

The second electrode 12 is placed at a distance from the first electrode 11 and, for example, has the shape of a ring extending circumferentially about the housing 10. The second electrode 12 is, for example, placed at a distance of about 1 cm from the tip 100 of the housing 10 at which the first electrode 11 is placed.

The implantable medical device 1, in the embodiment of FIGS. 2 and 3, in addition comprises a third electrode 13 placed at a far end 101 of the housing 10, the third electrode 13 serving as a sensing electrode for sensing signals indicative of cardiac activity in the far-field. In particular, a signal vector A arises between the third electrode 13 and the first electrode 11, the signal vector A picking up signals being indicative, for example, of atrial contractions and being denoted as far-field vector.

The electrodes 11, 12, 13 are in operative connection with the processing circuitry 15, the processing circuitry 15 being configured to cause the first electrode 11 and the second electrode 12 to emit a pacing signal for providing a stimulation at the ventricle. The processing circuitry 15 furthermore is configured to process signals received via the electrodes 11, 12, 13 to provide for a sensing of cardiac activity, in particular atrial and ventricular contractions.

If the implantable medical device 1 has the shape of a stimulation device comprising a generator 18 and a lead extending from the generator 18, as shown in the embodiment of FIG. 6, a similar electrode arrangement comprising, for example, three electrodes 11, 12, 13 may be arranged on a lead implanted in and extending into the right ventricle RV, as shown in FIG. 6, such that the above also applies to an embodiment of the implantable medical device 1 having a lead extending into the patient's heart. In this case, the processing circuitry may be part of the generator 18 and may be in operative connection with an electrode arrangement arranged on the lead.

In order to provide for a pacing in the ventricle in which the implantable medical device 1 is placed, in particular to enable a pacing in the VDD mode, a sensing of atrial activity is required to provide for detected atrial sense markers in order to time a pacing in the ventricle to obtain atrioventricular (AV) synchrony. For this, a far-field signal from in particular the right atrium RA (see FIGS. 1 and 6) shall be sensed in order to allow for a synchronous pacing in the right ventricle RV by means of the implantable medical device 1 being implanted on intracardiac tissue M in the right ventricle RV.

Figure 4:
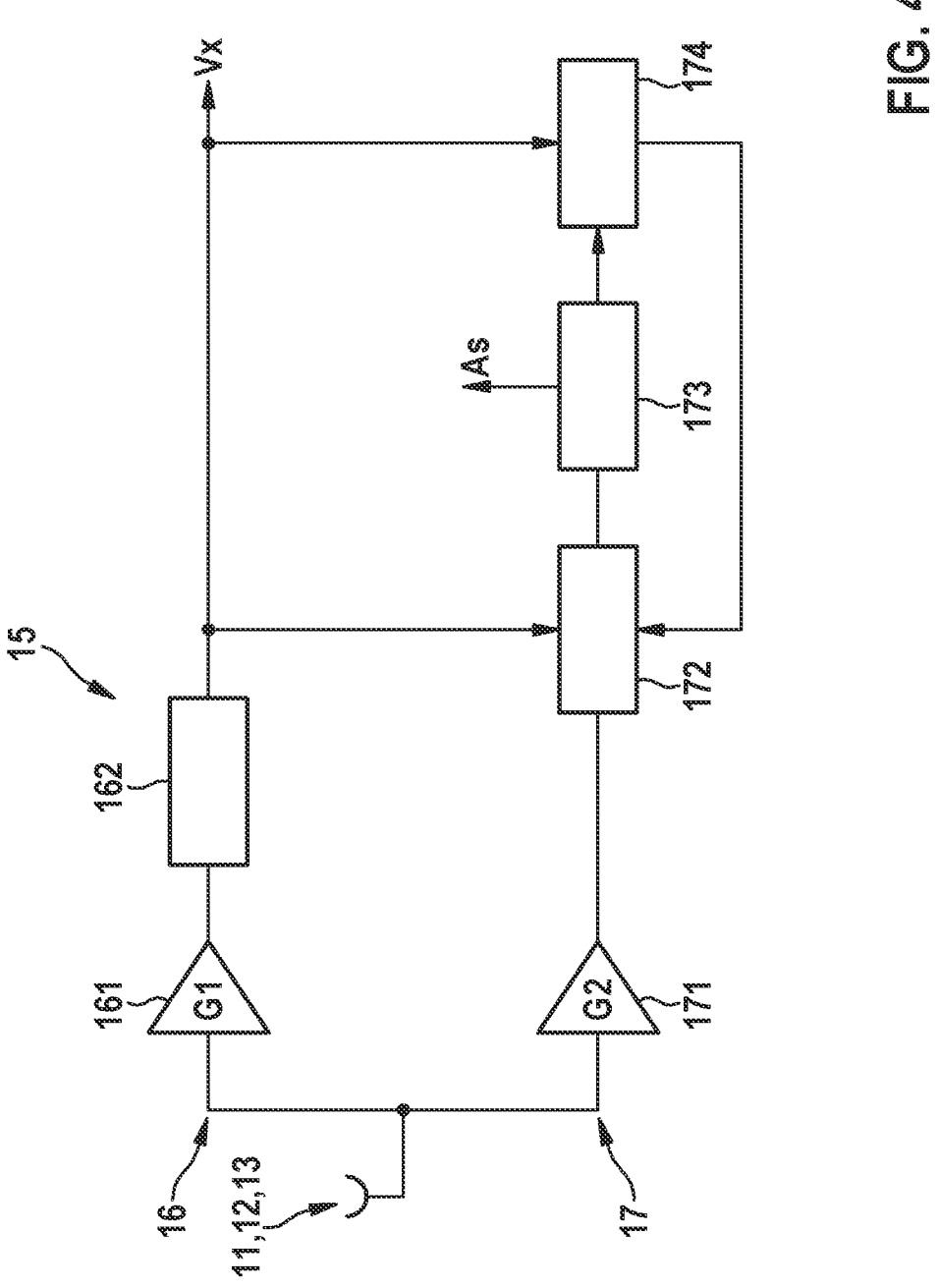
FIG. 4 shows a schematic view of a processing circuitry of an embodiment of an implantable medical device.

Referring now to FIG. 4, the processing circuitry 15 comprises, in one embodiment, two processing channels 16, 17 for processing different processing signals relating to ventricular activity and atrial activity. Herein, typically, an intracardiac electrogram (IEGM) contains a signal portions relating to ventricular activity (in particular a QRS wave) and atrial activity (in particular a P wave), signal portions relating to atrial activity however resulting from a far-field signal source and hence being far less pronounced and having a far smaller amplitude then signal portions relating to a ventricular activity in the near-field, i.e., arising in close proximity to the implanted implantable medical device 1. For this reason, the two processing channels 16, 17 are associated with different gains G1, G2, a first processing channel 16 serving to process a first processing signal to identify ventricular events Vx at a rather low gain G1 and a second processing channel 17 being configured to process a second processing signal to identify atrial events at a significantly higher gain G2.

In particular, the first processing channel 16 is connected to the electrode arrangement comprised of the electrodes 11, 12, 13, the first processing channel 16 being configured in particular to sense and process a signal received via the electrodes 11, 12 (near-field vector V in FIGS. 2 and 3). The first processing channel 16 comprises a first amplification stage 161 having a gain G1, the first amplification stage 161 being followed by a detection stage 162 which is configured to identify ventricular sense markers Vx from the first processing signal processed within the first processing channel 16.

The second processing channel 17 is likewise connected to the electrode arrangement comprised of electrodes 11, 12, 13, wherein the second processing channel 17 may in particular be configured to process a signal sensed via the far-field vector A, that is in between the electrodes 11, 13 placed at the tip 100 and the far end 101 of the housing 10 as illustrated in FIGS. 2 and 3. The second processing channel 17 comprises a second amplification stage 171 having a second gain G2, the second amplification stage 171 being followed by a processing stage 172 and a second detection stage 173.

The processing stage 172 serves to pre-process the second processing signal after amplification. The detection stage 173 in turn serves to evaluate and analyze the processed signal in order to identify atrial events within the second processing signal, the second processing channel 17 then outputting atrial sense markers As indicative of atrial events detected in the processed signal.

In addition, the processing circuitry 15 comprises a timing stage 174 which uses timing information received from the first processing channel 16 and the second processing channel 17 to provide for a pacing timing, in particular a VDD timing for achieving an atrial-ventricular synchronous pacing.

In order to identify and analyze atrial events, the gain G2 of the second processing channel 17 is (significantly) higher than the gain G1 of the first processing channel 16. This generally allows to analyze signal portions relating to atrial events, but makes it necessary to discern is such signal portions relating to atrial events from other signal portions, in particular signal portions relating to ventricular events Vx in the near-field and hence being far stronger than signal portions originating from atrial events in the far-field.

Within the processing stage 172, for example, a bandpass filtering, a windowing (e.g., partial blanking), a smoothing by means of a moving average filtering and a rectification may take place. A first or second order difference may be applied to remove a non-zero baseline while enhancing P wave defections.

Figures 5A, 5B:
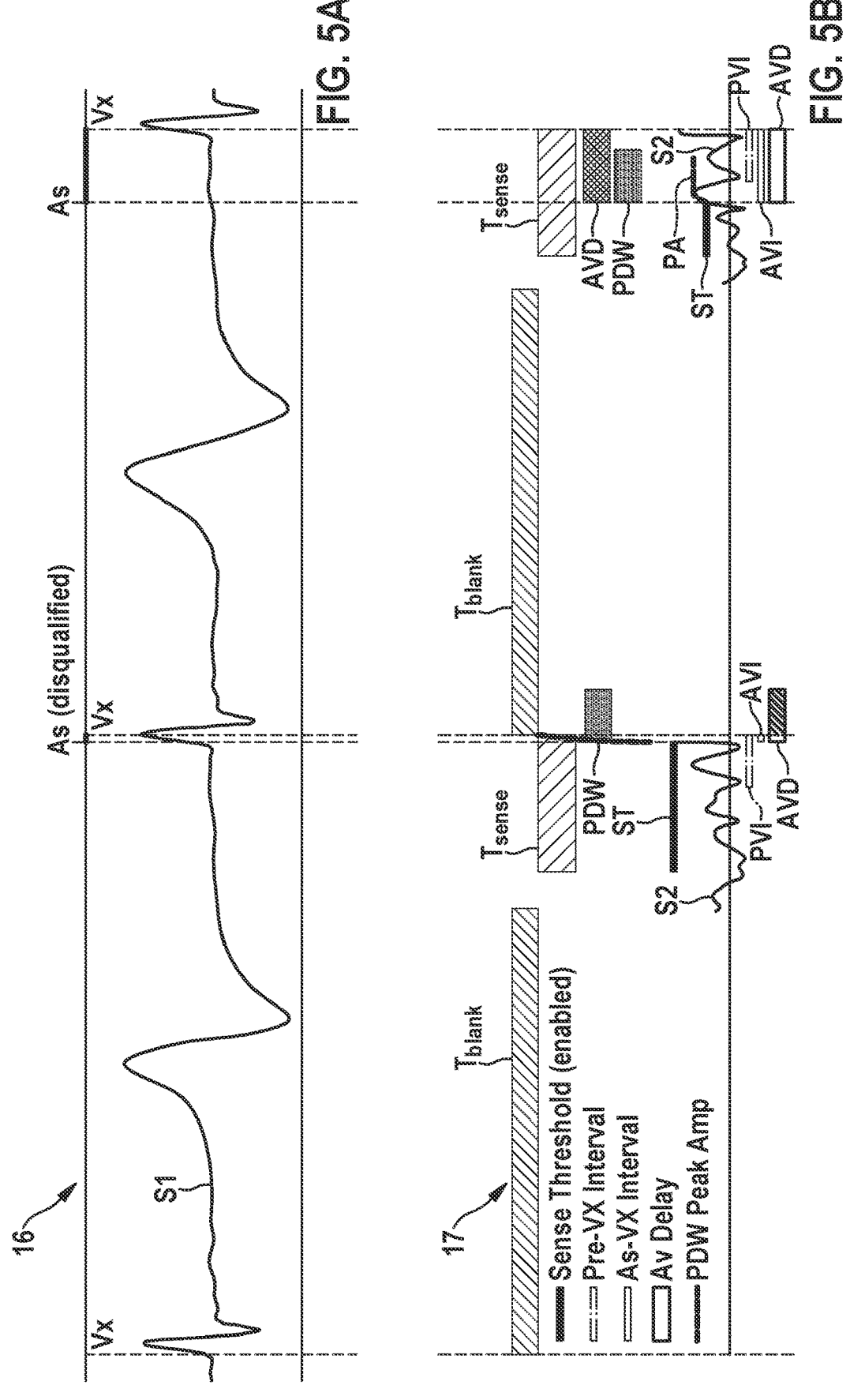
FIG. 5A shows a first processing signal in the shape of an intracardiac electrogram (IEGM) processed by a first processing channel of the processing circuitry.
FIG. 5B shows a second processing signal processed by a second processing channel of the processing circuitry.

FIGS. 5A and 5B show examples of signals S1, S2 as processed in the different processing channels 16, 17, FIG. 5A at the top showing a signal S1 as processed by the first processing channel 16 and FIG. 5B at the bottom showing a signal S2 as processed by the second processing channel 17. As a result of the processing, ventricular events Vx and atrial events As are identified and corresponding markers are output.

As apparent from FIG. 5B, the sensing of atrial events As uses a windowing scheme, employing in particular a blanking window $T_{blank}$ for blanking out signal portions of the signal S2 potentially relating to ventricular activity.

In particular, by means of the detection of ventricular events Vx in the first processing channel 16 a timing in between atrial events As and ventricular events Vx may be determined. According to such timing a start point and an end point of the blanking window $T_{blank}$ may be set, hence excluding signal portions from the processing which do not relate to atrial activity. Strong ventricular signals in this way may be suppressed such that signal portions relating to a ventricular activity may not interfere with a detection of atrial events As.

During the blanking window $T_{blank}$, the second processing channel 17 may be turned off. In particular, the amplification stage 171 of the second processing channel 17 may be switched of in order to save power.

Generally, a detection for atrial events As takes place outside of the blanking window $T_{blank}$. Herein, a detection window $T_{sense}$ for detecting atrial events As may start at the end of a prior blanking window $T_{blank}$. Alternatively, a detection window $T_{sense}$ may—as shown in the embodiment of FIG. 5B—have a delay with respect to the end of a prior blanking window $T_{blank}$, such that a signal processing within the second processing channel 17 starts at the end of a prior blanking window $T_{blank}$, a detection for atrial events As however starting only after a certain delay.

Generally, an atrial event As is assumed to be present if, in the detection window $T_{sense}$, the signal S2 crosses a sense threshold ST, as it is shown in FIG. 5B. The comparison may take place based on a rectification of the sense signal S2. Alternatively, a positive and negative sense threshold ST may be used, which may have the same value or may differ in their values.

As apparent from FIG. 5B, within the sense signal S2 signal portions may be present which are due to a near-field activity, in particular a ventricular activity, and may, for example, result from the beginning of a QRS waveform. It hence may occur that a threshold crossing may be due to near-field effects, as shown in FIG. 5B for the first atrial event As, the threshold crossing hence not being due to atrial activity. An atrial event As hence may be falsely detected.

For this, it herein is proposed to evaluate an atrial event As based on a timing with respect to a subsequent ventricular event Vx.

In particular, a scheme is proposed in which first a potentially present atrial event As is determined. Then a subsequent ventricular event Vx is determined. Based on the two events an atrial-ventricular interval AVI is determined. The atrial-ventricular interval AVI is compared to an exclusion interval PVI, also denoted as pre-Vx interval. If it is found that the atrial-ventricular interval AVI is smaller than the exclusion interval PVI, the atrial event As is disqualified and assumed to be invalid, as it is the case for the first atrial event As in FIG. 5B. Otherwise, if the atrial-ventricular interval AVI is larger than the exclusion interval PVI, as it is the case for the second atrial event As as shown in FIG. 5B, the atrial event As is assumed to be valid.

Hence, if it is found that a detected atrial event As lies too close to a subsequent ventricular event Vx, the atrial event As is disqualified and not used for further processing.

If an atrial event As qualifies as valid, as it is the case for the second atrial event As in FIG. 5B, the atrial event As is used for a further processing, in particular to update the sense threshold ST and to achieve an atrial-ventricular synchronous pacing.

In particular, the atrial event As is taken as that point in time at which the signal S2 crosses the sense threshold ST. At the time of the atrial event As a peak detection window PDW starts, and based on data recorded during that peak detection window PDW a peak amplitude PA is determined as the maximum signal value within the peak detection window PDW. This is indicated in FIG. 5B for the second atrial event As at the right.

Also, if the atrial event As is found to be valid, an atrial-ventricular delay AVD may be programmed as the internal delay from sensing the atrial event to initiating a pace.

If the peak detection window PDW overlaps with the exclusion interval PVI, the overlapping portion of the peak detection window PDW is excluded from processing in that data recorded within the overlapping portion is discarded and is not used for determining the peak amplitude PA (the overlapping portion may, for example, be identified subsequently to determining the subsequent ventricular event Vx; also the peak amplitude PA possibly is determined only after detection of the subsequent ventricular event Vx).

The peak amplitude PA is used to update the sense threshold ST. In particular, the processing circuitry 15 may be configured to update the sense threshold ST using an average threshold reference and a percentage ratio according to the formula $$ST=PC \cdot ATR(t),$$

where ST is the current sense threshold, PC is the percentage ratio, and ATR(t) is the average threshold reference for the current cycle t. The percentage ratio may lie, for example, in the range between 0% and 100%.

The average threshold reference may be computed and updated based on the peak amplitude PA according to the following equation:

$$ATR(t)=W \cdot PA(t-1)+(1-W) \cdot ATR(t-1),$$

where W indicates an update weight which determines how much the average threshold reference should change based on the previous peak amplitude, PA(t−1) is the peak amplitude as determined for the previous cycle t−1, and ATR(t−1) is the previous average threshold reference. For the actual cycle t the average threshold reference hence is determined based on the previously determined valid peak amplitude and on the previous average threshold reference for cycle t−1. For each cycle, hence, the average threshold reference is updated and computed anew, such that the average threshold reference is dynamically adjusted on a cycle-by-cycle basis.

If an atrial event As is found to be invalid because the atrial ventricular interval AVI is smaller than the exclusion interval PVI, no peak amplitude PA is determined and the sense threshold ST is not updated. In this way it is avoided that a false detection of an atrial event As may cause a false increase of the sense threshold ST and a subsequent capture loss of atrial activity.

Using atrial sense markers As output by the second processing channel 17, a ventricular synchronous pacing may be achieved. For this, it can be detected whether, following a detected atrial sense marker As, an intrinsic ventricular sense marker Vx occurs (output by to the first processing channel 16) within a predefined time delay window after the atrial sense marker As, in which case no stimulation is required. If no ventricular sense marker Vx is detected, a stimulation pulse may be emitted, causing a synchronous pacing at the ventricle.

Conversely, also an asynchronous pacing can be performed.

Utilizing a far-field electrical signal received by means of an implantable medical device can offer a superior detection of far-field events, in particular atrial events in case the implantable medical device is implanted into the ventricle. A tracking of far-field events by using and evaluating electrical signals may allow for an increased consistency and reliability in particular with respect to external factors such as posture and patient activity.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device
10 Body (housing)
100 Tip
101 Far end
11 First electrode (pacing electrode)
12 Second electrode (pacing ring)
13 Third electrode
14 Fixation device
15 Processing circuitry
16 Processing channel
161 Amplification stage
162 Detection stage
17 Processing channel
171 Amplification stage
172 Processing stage
173 Detection stage
174 Timing stage
18 Generator
A Signal vector (atrial/far-field vector)
As Atrial event (atrial sense marker)
AVD Atrial-ventricular delay
AVI Atrial-ventricular interval
AVN Atrioventricular node
G1, G2 Gain
H HIS bundle
LA Left atrium
LBB Left bundle branch LV Left ventricle
M Intracardiac tissue (myocardium)
P Signal vector (pacing vector)
PA Peak amplitude
PDW Peak detection window
PVI Exclusion interval (pre-Vx interval)
RA Right atrium
RBB Right bundle branch
RV Right ventricle
S1, S2 Signal
SAN Sinoatrial node
ST Sense threshold
$T_{blank}$ Blanking window
$T_{sense}$ Detection window
V Signal vector (ventricular/near-field vector)
Vx Ventricular event (ventricular sense marker)

The invention claimed is:

1. An implantable medical device configured to provide for an intracardiac function, the implantable medical device comprising:
a body;
a sensor arrangement arranged on the body and configured to receive cardiac sense signals; and
a processing circuitry operatively connected to the sensor arrangement, wherein the processing circuitry is configured to process cardiac sense signals received using the sensor arrangement:
to detect a signal deflection potentially indicative of an atrial event (As) caused by atrial activity to obtain an atrial detection,
to detect a signal deflection indicative of a ventricular event (Vx) caused by ventricular activity succeeding said atrial event (As),
to determine an atrial-ventricular interval (AVI) representing a time between the atrial detection and the ventricular event (Vx), and
to identify the atrial detection as valid or invalid by comparing said atrial-ventricular interval (AVI) to an exclusion interval (PVI) and identifying the atrial detection as valid if the atrial-ventricular interval (AVI) is longer than the exclusion interval (PVI) and as invalid if the atrial-ventricular interval (AVI) is shorter than the exclusion interval (PVI).

2. The implantable medical device according to claim 1, wherein said sensor arrangement is implemented by an electrode arrangement configured to receive electrical signals as cardiac sense signals.

3. The implantable medical device according to claim 1, wherein the body is formed by a lead which is connectable to a generator of the implantable medical device.

4. The implantable medical device according to claim 1, wherein the body is formed by a housing of a leadless pacemaker device.

5. The implantable medical device according to claim 1, wherein the processing circuitry is configured to determine a peak amplitude (PA) associated with the atrial detection if the atrial detection is identified as valid.

6. The implantable medical device according to claim 5, wherein the processing circuitry is configured to determine the peak amplitude (PA) associated with the atrial detection in a peak detection window (PDW) following the atrial detection.

7. The implantable medical device according to claim 6, wherein the processing circuitry is configured to determine whether a portion of the peak detection window (PDW)

overlaps with the exclusion interval (PVI) and to exclude data received within said portion when determining said peak amplitude (PA).

8. The implantable medical device according to claim 5, wherein the processing circuitry is configured to update, using the peak amplitude (PA), a sense threshold (ST) for detecting a subsequent atrial event (As).

9. The implantable medical device according to claim 8, wherein the processing circuitry is configured to update the sense threshold (ST) using an average threshold reference based on the equation $$ST(t)=PC{\cdot}ATR(t),$$

where ST(t) is the current sense threshold, PC is a percentage ratio, and ATR(t) is the current average threshold reference.

10. The implantable medical device according to claim 9, wherein the current average threshold reference is determined by the equation $$ATR(t)=W{\cdot}PA(t{-}1)+(1{-}W){\cdot}ATR(t{-}1),$$

where W indicates an update weight, PA(t−1) is the peak amplitude as determined for the previous cycle t−1, and ATR (t−1) is the previous average threshold reference.

11. The implantable medical device according to claim 1, wherein the processing circuitry is configured to count a cardiac cycle during which the atrial detection occurred as a missed cycle if the atrial detection is identified as invalid.

12. The implantable medical device according to claim 1, wherein the processing circuitry comprises a first processing channel having a first gain (G1) for processing a first signal derived from cardiac sense signals received via the sensor arrangement and a second processing channel having a second gain (G2) for processing a second processing signal derived from cardiac sense signals received via the sensor arrangement, the second gain (G2) being higher than the first gain (G1).

13. The implantable medical device according to claim 12, wherein the processing circuitry is configured to process the first processing signal to detect a ventricular activity and the second processing signal to detect an atrial activity.

14. Method for operating an implantable medical device for providing for an intracardiac function, comprising:

receiving, using a sensor arrangement arranged on a body of the implantable medical device, cardiac sense signals; and processing, using a processing circuitry operatively connected to the sensor arrangement, cardiac sense signals received using the sensor arrangement:

to detect a signal deflection potentially indicative of an atrial event (As) caused by atrial activity to obtain an atrial detection, to detect a signal deflection indicative of a ventricular event (Vx) caused by ventricular activity succeeding said atrial detection, to determine an atrial-ventricular interval (AVI) representing a time between the atrial detection and the ventricular event (Vx), and to identify the atrial detection as valid or invalid by comparing said atrial-ventricular interval (AVI) to an exclusion interval (PVI) and identifying the atrial detection as valid if the atrial-ventricular interval (AVI) is longer than the exclusion interval (PVI) and as invalid if the atrial-ventricular interval (AVI) is shorter than the exclusion interval (PVI).

\* \* \* \* \*